(12) United States Patent
Hubalek et al.

(10) Patent No.: US 8,883,722 B2
(45) Date of Patent: *Nov. 11, 2014

(54) HUMAN INSULIN CONTAINING ADDITIONAL DISULFIDE BONDS

(75) Inventors: Frantisek Hubalek, Herlev (DK); Tine Nygaard Vinther, Frederiksberg C. (DK); Thomas Boerglum Kjeldsen, Virum (DK); Svend Ludvigsen, Lynge (DK)

(73) Assignee: Novo Nordisk A/S, Bagsvaerd (NO)

( * ) Notice: Subject to any disclaimer, the term of this patent is extended or adjusted under 35 U.S.C. 154(b) by 0 days.

This patent is subject to a terminal disclaimer.

(21) Appl. No.: 13/805,494

(22) PCT Filed: Jun. 21, 2011

(86) PCT No.: PCT/EP2011/060295
§ 371 (c)(1),
(2), (4) Date: Mar. 6, 2013

(87) PCT Pub. No.: WO2011/161083
PCT Pub. Date: Dec. 29, 2011

(65) Prior Publication Data
US 2013/0178414 A1 Jul. 11, 2013

Related U.S. Application Data

(60) Provisional application No. 61/359,127, filed on Jun. 28, 2010.

(30) Foreign Application Priority Data

Jun. 23, 2010 (EP) .................................... 10167036

(51) Int. Cl.
*A61K 38/28* (2006.01)
*C07K 14/62* (2006.01)

(52) U.S. Cl.
CPC ..................................... *C07K 14/62* (2013.01)
USPC ............... 514/5.9; 514/6.1; 514/6.2; 530/303

(58) Field of Classification Search
USPC ......................................................... 514/5.9
See application file for complete search history.

(56) References Cited

U.S. PATENT DOCUMENTS

2012/0184488 A1 7/2012 Weiss

FOREIGN PATENT DOCUMENTS

| CN | 101541830 A | 9/2009 |
|---|---|---|
| WO | 92/00321 A1 | 1/1992 |
| WO | 2005/012347 A2 | 2/2005 |
| WO | 2007/135117 A2 | 11/2007 |
| WO | 2008/034881 A1 | 3/2008 |
| WO | 2009087081 A2 | 7/2009 |
| WO | 2009/112583 A2 | 9/2009 |
| WO | 2010/066636 A1 | 6/2010 |

OTHER PUBLICATIONS

Goeddel et al., PNAS, 76: 106-110,1979.*
Brems et al., "Improved Insulin Stability Through Amino Acid . . . ", Protein Engineering, vol. 5(6), pp. 519-525 (1992).
Brange et al., "Insulin Structure and Stability," Pharm. Biotechnology, vol. 5, pp. 315-350 (1993).
Mansfeld et al., "Extreme Stabilization of a Thermolysin-Like . . . ", J. Biol. Chem, vol. 272(17), pp. 11152-11156 (1997).
Matsumura et al., "Stabilization of Phase T4 Iysozyme by Engineered . . . ", Proc. Natl Acad Sci USA, vol. 86, pp. 6562-6566 (1989).
Wetzel et al., "Disulfide Bonds and Thermal Stability in T4 Lysozyme . . . ", Proc Natl Acad Sci USA, vol. 85, pp. 401-405 (1988).
Almog et al., "Structural Basis of Thermostability," J. Biol. Chem., vol. 277(30), pp. 27553-27558 (2002).
Arnold et al., "Natural and Engineered Ribonucleases as . . . ", Biotechnol Letters, vol. 28, pp. 1615-1622 (2006).
Pace, C. N., "Conformational Stability of Globular Proteins," Trends Biochem Sci, vol. 15(1), pp. 14-17 (1990).
McAuley et al., "Contributions of Disulfide Bond to the Structure . . . ", Protein Science, vol. 17(1), pp. 95-106 (2008).
Hagihara et al., "Stabilization of an Immunoglobulin Fold Domain," J. Biol Chem, vol. 282(50), pp. 36489-36495 (2007).
Creighton, Thomas E., "Protein Folding Pathways Determined Using . . . ", Bioessays, vol. 14(3), pp. 195-199 (1992).
Clarke et al., "The Effects of Disulfide Bonds on the Denatured . . . ", Protein Sci., vol. 9, pp. 2394-2404 (2000).
Clarke et al., "Engineered Disulfide Bonds as Probes of the . . . ", Biochemistry, vol. 32(16), pp. 4322-4329 (1993).
Ikeguchi et al., "Contribution of the 6-120 Disulfide Bond of a . . . ", Biochemistry, vol. 31(50), pp. 12695-12700 (1992).
Dolginova et al., "Chemical Modification of Torpedo . . . ", Biochemistry, vol. 31, pp. 12248-12254 (1992).
Vogl et al., "Mechanism of Protein Stabilization by Disulfide," J. Mol. Biol., vol. 254(3), pp. 481-496 (1995).
Landenstein R. et al., "Protein Disulfides and Protein Disulfide . . . ", FEBS, vol. 273, pp. 4170-4185 (2006).
Mallick et al., "Genomic Evidence That the Intracellular Proteins . . . ", Proc. Natl Acad Sci USA, vol. 99(19), pp. 9679-9684 (2002).
Peer Bork, Power and Pitfalls in Sequence Analysis: The 70% Hurdle, Genome Research, 2000, 398-400, vol. 10.
Eliane Lazar et al., Transforming Growth Factor alpha : Mutation of Aspartic Acid 47 and Leucine 48 Results in different Biological Activities, Molecular and Cellular Biology, 1988, vol. 8,1247-1252.
Wilson H. Burgess et al., Possible dissociation of the Heparin-binding and Mitogenic Activities of Heparin-binding (Acidic Fibroblast) Growth Factor-1 from its Receptor-binding Activities by Site-directed Mutagenesis of a Single Lysine Residue,The Journal of Cell Biology, 1990, 2129-2138, vol. 111.
James U. Bowie et al., Deciphering the message in protein sequences: Tolerance to Amino Acid Substitutions, Science, 1990, 1306-1310, vol. 247.
Chang, B.S. et al., Practical Approaches to Protein Formulation Development, Rational Design of Stable Protein Formulations-theory and practice (J.F. Carpenter and M. C. Manning eds.), 2002, 1-28.

* cited by examiner

*Primary Examiner* — Gyan Chandra
(74) *Attorney, Agent, or Firm* — Jianjie Hu (57) ABSTRACT

The present invention is related to human insulin containing additional disulfide bonds and methods of making such.

12 Claims, 3 Drawing Sheets

Fig. 3

HUMAN INSULIN CONTAINING ADDITIONAL DISULFIDE BONDS

CROSS-REFERENCE TO RELATED APPLICATIONS

This application is a 35 U.S.C. §371 National Stage application of International Application PCT/EP2011/060295, filed Jun. 21, 2011, which claimed priority of European Patent Application 10167036.2, filed Jun. 23, 2010; this application claims priority under 35 U.S.C. §119 of U.S. Provisional Application 61/359,127, filed Jun. 28, 2010.

FIELD OF THE INVENTION

The present invention is related to human insulin and desB30 human insulin containing additional disulfide bonds and methods of making such.

BACKGROUND OF THE INVENTION

Diabetes mellitus is a metabolic disorder in which the ability to utilize glucose is partly or completely lost. In the treatment of diabetes mellitus, many varieties of insulin formulations have been suggested and used, such as regular insulin, isophane insulin (designated NPH), insulin zinc suspensions (such as Semilente®, Lente®, and Ultralente®), and biphasic isophane insulin.

Human insulin consists of two polypeptide chains, the A and B chains which contain 21 and 30 amino acid residues, respectively. The A and B chains are interconnected by two disulfide bridges. Insulin from most other species is similar, but may contain amino acid substitutions in some positions. Within the last decade a number of human insulin analogues have been developed. They are designed for particular profiles of action, i.e. fast acting or prolonged action. Commercially available products comprising such insulin analogues include Levemir®, NovoRapid®, Humalog®, Apidra® and Lantus®.

Human insulin is rapidly degraded in the lumen of gastrointestinal tract by the action of multiple proteases limiting its absorption into circulation. Insulin analogues that are hydrophilic and stabilized towards proteolytic degradation show higher bioavailability in animal models when compared to native insulin.

Incorporation of disulfide bonds into proteins is one of nature's ways of improving protein stability; a correlation between the abundance of disulfide bonds and the maximum growth temperature among thermophilic organisms has been found, implicating the importance of disulfide bonds in protein stabilization in high temperature environments (Mallick P, et al, 2002, Proc. Natl. Acad. Sci. USA, 99, 9679-9684; Ladenstein R, et al, 2006, FEBS J., 273, 4170-4185). There are also many examples of disulfide bonds being successfully engineered into proteins with concomitant increases in stability. One of the largest stabilizations was achieved for RNAse barnase (Clarke J., Fersht A., 1993, Biochem., 32, 4322-4329). Such stabilization is brought about by increasing the activation energy required for unfolding or by constraining the unfolded conformations of the protein and thereby decreasing their conformational entropy (Pace C. N., 1990, Trends Biol. Sci.,14-17). However, much more needs to be learned in this emerging area of research. To date, there are no reports of engineered disulfide bonds in insulin.

There is still a need for novel human insulin analogues which are stable.

SUMMARY OF THE INVENTION

The present invention is related to human insulin analogues having two or more cysteine substitutions, where the three disulfide bonds of human insulin are retained and the sites of cysteine substitutions are chosen in such a way that the introduced cysteine residues are placed in the three dimensional structure of the folded insulin analogue to allow for the formation of one or more additional disulfide bonds not present in human insulin.

In one aspect a human insulin of the invention is obtained, wherein the sites of cysteine substitutions are chosen in such a way that (1) the introduced cysteine residues are placed in the three dimensional structure of the folded insulin analogue to allow for the formation of one or more additional disulfide bonds not present in human insulin, and (2) the human insulin analogue retains the desired biological activities associated with human insulin.

In one aspect a human insulin of the invention is obtained—wherein the sites of cysteine substitutions are chosen in such a way that (1) the introduced cysteine residues are placed in the three dimensional structure of the folded insulin analogue to allow for the formation of one or more additional disulfide bonds not present in human insulin, (2) the human insulin analogue retains the desired biological activities associated with human insulin, and (3) the human insulin analogue has increased physical stability relative to human insulin and/or parent insulin.

In one aspect a human insulin of the invention is obtained, wherein the sites of cysteine substitutions are chosen in such a way that (1) the introduced cysteine residues are placed in the three dimensional structure of the folded insulin analogue to allow for the formation of one or more additional disulfide bonds not present in human insulin, (2) the human insulin analogue retains the desired biological activities associated with human insulin, and (3) the human insulin analogue is stabilized against proteolytic degradation.

Herein is also described a method for stabilizing human insulin comprising substituting two or more amino acids of human insulin or desB30 human insulin with cysteine residues, wherein the three disulfide bonds of human insulin are retained and the sites of cysteine substitutions are chosen in such a way that the introduced cysteine residues are placed in the three dimensional structure of the folded insulin analogue to allow for the formation of one or more additional disulfide bonds not present in human insulin, whereby a human insulin analogue comprising one or more additional disulfide bonds not present in human insulin is obtained.

DESCRIPTION OF THE INVENTION

In the present invention novel human insulin analogues are presented wherein disulfide bonds are engineered into the insulin.

In one aspect a human insulin analogue according to the invention has two or more cysteine substitutions and the three disulfide bonds of human insulin are retained.

In one aspect of the invention, the sites of cysteine substitutions are chosen in such a way that the introduced cysteine residues are placed in the three dimensional structure of the folded human insulin analogue to allow for the formation of one or more additional disulfide bonds not present in human insulin.

It has by the inventors been found that the human insulin analogues according to the invention have improved physical stability. It has thus been found that the tendency of the human insulin analogues according to the invention to form biologically inactive and/or insoluble aggregates of the human insulin analogues is reduced for example as a result of exposure of the human insulin analogues to thermo-mechanical stresses and/or interaction with interfaces and surfaces that are destabilizing, such as hydrophobic surfaces and interfaces.

The human insulin analogues according to the invention bind to the insulin receptor. It has thus surprisingly been found by the inventors that the human insulin analogues according to the invention have both improved physical stability and retain binding to the insulin receptor.

In one aspect the human insulin analogues of the invention are stabilized against proteolytic degradation, i.e. against rapid degradation in the gastro intestinal (GI) tract or elsewhere in the body. In one aspect the human insulin analogues of the invention are stabilized against proteolytic degradation relative to human insulin or desB30 human insulin.

A human insulin analogue which is stabilized against proteolytic degradation is herein to be understood as a human insulin analogue, which is subjected to slower degradation by one or more proteases relative to human insulin. In one embodiment a human insulin analogue according to the invention is subjected to slower degradation by one or more proteases relative to human insulin. In a further embodiment of the invention a human insulin analogue according to the invention is stabilized against degradation by one or more enzymes selected from the group consisting of: pepsin (such as e.g. the isoforms pepsin A, pepsin B, pepsin C and/or pepsin F), chymotrypsin (such as e.g. the isoforms chymotrypsin A, chymotrypsin B and/or chymotrypsin C), trypsin, Insulin-Degrading Enzyme (IDE), elastase (such as e.g. the isoforms pancreatic elastase I and/or II), carboxypeptidase (e.g. the isoforms carboxypeptidase A, carboxypeptidase A2 and/or carboxypeptidase B), aminopeptidase, cathepsin D and other enzymes present in intestinal extracts derived from rat, pig or human.

In one embodiment a human insulin analogue according to the invention is stabilized against degradation by one or more enzymes selected from the group consisting of: chymotrypsin, trypsin, Insulin-Degrading Enzyme (IDE), elastase, carboxypeptidases, aminopeptidases and cathepsin D. In a further embodiment a human insulin analogue according to the invention is stabilized against degradation by one or more enzymes selected from the group consisting of: chymotrypsin, carboxypeptidases and IDE. In a yet further embodiment a human insulin analogue according to the invention is stabilized against degradation by one or more enzymes selected from: chymotrypsin and IDE. In a yet further embodiment a human insulin analogue according to the invention is stabilized against degradation by one or more enzymes selected from: chymotrypsin and carboxypeptidases.

A "protease" or a "protease enzyme" is a digestive enzyme which degrades proteins and peptides and which is found in various tissues of the human body such as e.g. the stomach (pepsin), the intestinal lumen (chymotrypsin, trypsin, elastase, carboxypeptidases, etc.) or mucosal surfaces of the GI tract (aminopeptidases, carboxypeptidases, enteropeptidases, dipeptidyl peptidases, endopeptidases, etc.), the liver (Insulin degrading enzyme, cathepsin D etc), and in other tissues.

T½ may be determined as a measure of the proteolytical stability of a human insulin analogue according to the invention towards protease enzymes such as chymotrypsin, pepsin and/or carboxypeptidase A or towards a mixture of enzymes such as tissue extracts (from liver, kidney, duodenum, jejunum, ileum, colon, stomach, etc.). In one embodiment of the invention T½ is increased relative to human insulin. In a further embodiment T½ is increased relative to the parent insulin. In a yet further embodiment T½ is increased at least 2-fold relative to the parent insulin. In a yet further embodiment T½ is increased at least 3-fold relative to the parent insulin. In a yet further embodiment T½ is increased at least 4-fold relative to the parent insulin. In a yet further embodiment T½ is increased at least 5-fold relative to the parent insulin. In a yet further embodiment T½ is increased at least 10-fold relative to the parent insulin.

In one aspect, the human insulin analogues according to the invention have improved chemical stability. In one aspect, the human insulin analogues according to the invention have improved physical stability. In one aspect, the human insulin analogues according to the invention have improved chemical and physical stability.

In one aspect, a human insulin analogue according to the invention has improved chemical and/or physical stability relative to human insulin. In one aspect, a human insulin analogue according to the invention has improved chemical and/or physical stability relative to the parent insulin.

The term "physical stability" as used herein refers to the tendency of the human insulin analogue to form biologically inactive and/or insoluble aggregates of the human insulin analogue as a result of exposure of the human insulin analogue to thermo-mechanical stresses and/or interaction with interfaces and surfaces that are destabilizing, such as hydrophobic surfaces and interfaces. Physical instability thus involves conformational changes relative to human insulin, which includes loss of higher order structure, aggregation, fibrillation, precipitation and/or adsorption to surfaces. Peptides such as insulin are known to be prone to instability due to e.g. fibrillation. Physical stability of a solution comprising the human insulin analogue may be evaluated by conventional means of e.g. visual inspection, nephelometry and/or turbidity measurements after exposing the solution filled in suitable containers (e.g. cartridges or vials) to mechanical/physical stress (e.g. agitation) at different temperatures for various time periods. Visual inspection of the solution is performed in a sharp focused light with a dark background. The turbidity of the solution is characterized by a visual score ranking the degree of turbidity for instance on a scale from 0 to 3 (a solution showing no turbidity corresponds to a visual score 0, and a solution showing visual turbidity in daylight corresponds to visual score 3). A solution is classified physical unstable with respect to protein aggregation, when it shows visual turbidity in daylight. Alternatively, the turbidity of the solution can be evaluated by simple turbidity measurements well-known to the skilled person. Physical stability of the human insulin analogue can also be evaluated by using a spectroscopic agent or probe of the conformational status of the human insulin analogue. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially nonfluorescent at the wavelengths. Physical stability of the human insulin analogues of the invention may e.g. be determined as described in example 13.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the human insulin analogue as used herein refers to chemical covalent changes in the protein structure leading to formation of chemical degradation products with potential less biological potency and/or potential increased immunogenic properties compared to the native protein structure and involves avoidance of degradation of covalent bonds, such as hydrolysis, racemization, oxidation or crosslinking. Various chemical degradation products can be formed depending on the type and nature of the native protein and the environment to which the human insulin analogue is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutamine or asparagine residues is hydrolysed to form a free carboxylic acid. Asparagine and aspartic acid residues may further form isoAsp degradation products. Other degradations pathways involves formation of high molecular weight transformation products where two or more protein molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) and racemization can be mentioned as another variant of chemical degradation. The chemical stability of the human insulin analogue can be evaluated by measuring the amount of the chemical degradation products at various time-points after exposure to different environmental conditions (the formation of degradation products can often be accelerated by for instance increasing temperature). The individual degradation products are often determined by separation of the degradation products depending on molecule size and/or charge e.g. using a combination of chromatographic (e.g. SEC-HPLC, RP-HPLC or IE-HPLC) and spectroscopic methods (various mass spectrometry methods) sometimes in combinations with chemical/enzymatic fragmentation.

In one embodiment, the human insulin analogue of the invention has improved chemical stability relative to that of human insulin and/or desB30 human insulin when tested as described in the examples.

In one embodiment, the human insulin analogue of the invention has increased hydrophilicity relative to that of human insulin and/or desB30 human insulin when tested for hydrophobicity as known by the skilled person and e.g. described in example 14.

In one embodiment, the human insulin analogue of the invention has little or no tendency to aggregate. The aggregation tendency is preferably significantly improved relatively to the aggregation tendency of human insulin and/or desB30 human insulin when tested in a thioflavin assay.

A human insulin analogue according to the invention may have substantially the same or increased in vivo potency relative to the parent insulin. In one aspect a human insulin analogue of the invention has substantially the same in vivo potency relative to the parent insulin. In one aspect a human insulin analogue of the invention has increased in vivo potency relative to the parent insulin.

Standard assays for measuring insulin in vivo potency are known to the person skilled in the art and include assays described in the examples, such as; Potency of human insulin analogues of the invention relative to human insulin, intravenous steady-state clamp assays such as rat pharmacokinetics and rat PK following intraintestinal injection, blood glucose lowering effect and intravenous rat PK assays.

A human insulin analogue according to the invention may have substantially the same or increased in vitro potency relative to the parent insulin. In one aspect a human insulin analogue of the invention has substantially the same in vitro potency relative to the parent insulin. In one aspect a human insulin analogue of the invention has increased in vitro potency relative to the parent insulin.

Standard assays for measuring insulin in vitro potency are known to the person skilled in the art and include inter alia the below in vitro assays:
(1) insulin radioreceptorassays, in which the relative potency of an insulin is defined as the ratio of insulin to insulin analogue required to displace 50% of $^{125}$I-insulin specifically bound to insulin receptors present on cell membranes, e.g. a rat liver plasma membrane fraction;
(2) lipogenesis assays, performed e.g. with rat adipocytes, in which relative insulin potency is defined as the ratio of insulin to insulin analogue required to achieve 50% of the maximum conversion of [3-$^3$H] glucose into organic-extractable material (i.e. lipids); and
(3) glucose oxidation assays in isolated fat cells in which the relative potency of the human insulin analogue is defined as the ratio of insulin to insulin analogue to achieve 50% of the maximum conversion of glucose-1-[$^{14}$C] into [$^{14}$CO$_2$].

In one aspect, a human insulin analogue according to the invention has improved thermodynamic stability such as e.g. folding stability, conformational stability and/or higher melting temperature.

When used herein a human insulin analogue is said to have improved "thermodynamic stability" if denaturation of said human insulin analogue requires higher stress level such as higher temperature and/or higher concentration of denaturation agent in comparison to human/desB30 human insulin.

Conformational stability may be evaluated by circular dichroism and NMR as e.g. described by Hudson and Andersen, Peptide Science, vol 76 (4), pp. 298-308 (2004). Melting temperature is understood as the temperature at which an insulin structure is reversibly or irreversibly changed. Higher melting temperature corresponds to more stable structures. Melting temperature can be determined e.g. by evaluating conformational stability by circular dichroism and/or NMR as a function of temperature or by differential scanning calorimetry. Thermodynamic stability can also be determined by CD spectroscopy and or NMR in the presence of increasing concentration of denaturation agent, such as for example guanidinium hydrochloride. Free energy of unfolding as described previously (Kaarsholm, N. C., et al, 1993, Biochemistry, 32, 10773-8) can be determined from such experiments. Upon protein denaturation, negative CD in the far UV range (240-218-nm) gradually diminishes, consistent with the loss of ordered secondary structure that accompanies protein unfolding (Holladay et al., 1977, Biochim. Biophys. Acta, 494, 245-254; Melberg and Johnson, 1990, Biochim. Biophys. Acta, 494, 245-254). The insulin CD spectrum in the near UV range (330-250-nm) reflects the environment of the tyrosine chromophore with contributions from the disulfide bonds (Morris et al., 1968, Biochim. Biophys. Acta., 160, 145-155; Wood et al., 1975, Biochim. Biophys. Acta, 160, 145-155; Strickland & Mercola, 1976, Biochemistry, 15, 3875-3884). The free energy of unfolding of insulin was previously calculated from such studies to be 4.5 kcal/mol (Kaarsholm, N. C., et al, 1993, Biochemistry, 32, 10773-8).

Insulin CD spectrum in the near UV range (330-250-nm) reflects the environment of the tyrosine chromophore with contributions from the disulfide bonds. Since tyrosine residues are part of the insulin's dimer surface, changes in molar elipticity at this region (especially at 276 nm) reflect on insulin's association state. Another way to measure insulin's association state is by application of size-exclusion chromatography under non-dissociating conditions as known in the art and described in the examples.

Disulfide bonds are derived by the coupling of two thiol groups and herein to be understood as the linkage between two sulfur atoms, i.e. a structure having the overall connectivity R—S—S—R. Disulfide bonds may also be called connecting disulfide bonds, SS-bonds or disulfide bridges. A disulfide bond is created by the introduction of two cysteine amino acid residues to a peptide with subsequent oxidation of the two thiol groups to a disulfide bond. Such oxidation can be performed chemically (as known by persons skilled in the art) or can happen during insulin expression in e.g. yeast.

When introducing cysteine residues into the parent insulin, the cysteine residues are placed in the three dimensional structure of the folded insulin analogue to allow for the formation of one or more additional disulfide bonds not present in human insulin. For example, if placing two new cysteine residues, the proximity of the new cysteine residues in the three dimensional structure is such that a disulfide bond can be formed between the two new cysteine residues.

In one aspect of the invention a human insulin analogue which has two or more cysteine substitutions is provided, where the three disulfide bonds of human insulin are retained.

With the term "cysteine substitution" is herein meant replacing an amino acid in human insulin with a cysteine. For example, isoleucine in position 10 in the A chain (IleA10) and glutamine in position 4 of the B chain of human insulin (GlnB4) may each be replaced by a cysteine residue.

The term "human insulin" as used herein means the human insulin hormone whose two dimensional and three dimensional structures and properties are well-known. The three dimensional structure of human insulin has been e.g. determined by NMR and X-ray crystallography under many different conditions and many of these structures are deposited in the Protein data bank (http://www.rcsb.org). Non-limiting examples of a human insulin structure is the T6 structure (http://www.rcsb.org/pdb/explore.do?structureId=1MSO) and the R6 structure (http://www.rcsb.org/pdb/explore.do?structureId=1EV3). Human insulin has two polypeptide chains, named the A-chain and the B-chain. The A-chain is a 21 amino acid peptide and the B-chain is a 30 amino acid peptide, the two chains being connected by disulfide bonds: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain. Thus, a human insulin analogue where "the three disulfide bonds of human insulin are retained" is herein understood as a human insulin analogue comprising the three disulfide bonds of human insulin, i.e. a disulfide bond between the cysteine in position 7 of the A-chain and the cysteine in position 7 of the B-chain, a disulfide bond between the cysteine in position 20 of the A-chain and the cysteine in position 19 of the B-chain and a disulfide bond between the cysteines in position 6 and 11 of the A-chain.

In the human body, the insulin hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

In one aspect of the invention a human insulin analogue which has two or more cysteine substitutions is provided, where the three disulfide bonds of human insulin are retained, and wherein at least one amino acid residue in a position selected from the group consisting of A9, A10 and A12 of the A-chain is substituted with a cysteine, at least one amino acid residue in a position selected from the group consisting of B1, B2, B3, B4, B5 and B6 of the B-chain is substituted with a cysteine, and optionally the amino acid in position B30 is deleted. In one aspect of the invention, the amino acid residue in position A10 of the A-chain is substituted with a cysteine, at least one amino acid residue in a position selected from the group consisting of B1, B2, B3, and B4 of the B-chain is substituted with a cysteine, and optionally the amino acid in position B30 is deleted. In one aspect of the invention, the amino acid residue in position A10 of the A-chain is substituted with a cysteine, at least one amino acid residue in a position selected from the group consisting of B3 and B4 of the B-chain is substituted with a cysteine, and optionally the amino acid in position B30 is deleted. In one aspect of the invention, the amino acid residue in position A10 of the A-chain is substituted with a cysteine, the amino acid residue in position B3 of the B-chain is substituted with a cysteine, and optionally the amino acid in position B30 is deleted. In one aspect of the invention, the amino acid residue in position A10 of the A-chain is substituted with a cysteine, the amino acid residue in B4 of the B-chain is substituted with a cysteine, and optionally the amino acid in position B30 is deleted.

In one aspect, insulin analogues according to the invention are obtained, wherein the amino acid in position B30 is deleted.

An additional disulfide bond obtained by the invention may be connecting two cysteines of the same chain, i.e. two cysteines in the A-chain or two cysteines in the B-chain of the insulin, or connecting a cysteine in the A-chain with a cysteine in the B-chain of the insulin. In one aspect, a human insulin analogue according to the invention is obtained, wherein at least one additional disulfide bond is connecting two cysteines in the A-chain or connecting two cysteines in the B-chain. In one aspect, a human insulin analogue according to the invention is obtained, wherein at least one additional disulfide bond is connecting a cysteine in the A-chain with a cysteine in the B-chain.

When used herein the term "additional disulfide bonds" means one or more disulfide bonds which are not present in human insulin.

In one aspect of the invention, cysteines are substituted into two positions of the human insulin analogue, where the positions are selected from the group consisting of:
A10C, B1 C;
A10C, B2C;
A10C, B3C;
A10C, B4C;
A10C, B5C; and
B1C, B4C.

In one aspect of the invention, cysteines are substituted into two positions of the human insulin analogue, where the positions are selected from the group consisting of:
A10C, B1C;
A10C, B2C;
A10C, B3C;
A10C, B4C; and
B1C, B4C.

In one aspect of the invention, cysteines are substituted into two positions of the human insulin analogue, where the positions are selected from the group consisting of:
A10C, B1C;
A10C, B2C;
A10C, B3C; and
A10C, B4C.

In one aspect of the invention, cysteines are substituted into two positions of the human insulin analogue, where the positions are selected from the group consisting of:
S10C, B3C; and
A10C, B4C.

In one aspect of the invention, cysteines are substituted into two positions of the human insulin analogue, where the positions are A10C and B3C.

In one aspect of the invention, cysteines are substituted into two positions of the human insulin analogue, where the positions are A10C and B4C.

In one aspect of the invention, a human insulin analogue is obtained which comprises two cysteine substitutions resulting in one additional disulfide bond relative to human insulin.

The terms "an insulin" and "the insulin" according to the invention are herein to be understood as human insulin or desB30 human insulin.

The term "insulin peptide" as used herein means a peptide which is either human insulin or an analogue or a derivative thereof with insulin activity.

The term "parent insulin" as used herein is intended to mean an insulin before any cysteine substitutions according to the invention have been applied thereto. In one aspect the parent insulin is human insulin or desB30 human insulin. In one aspect the parent insulin is desB30 human insulin. In one aspect the parent insulin is human insulin.

In one aspect of the invention, the sites of cysteine substitutions are chosen in such a way that the human insulin analogue retains the desired biological activities associated with human insulin. Desired biological activities are known to the person skilled in the art and e.g. include binding to the insulin receptor, binding to the IGF-1 (Insulin Growth Factor 1) receptor, in vitro potency (measure of lipogenesis, glycogen synthesis), in vivo potency (steady state clamp, PK and PD experiments) as e.g. described in the Examples.

In one aspect, human insulin analogues according to the invention are obtained, wherein the receptor binding to the insulin receptor is at least 1% of the receptor binding of human insulin to the insulin receptor. In one aspect, the receptor binding to the insulin receptor is at least 3% of the receptor binding of human insulin to the insulin receptor. In one aspect, the receptor binding to the insulin receptor is at least 5% of the receptor binding of human insulin to the insulin receptor. In one aspect, the receptor binding to the insulin receptor is at least 10% of the receptor binding of human insulin to the insulin receptor. In one aspect, the receptor binding to the insulin receptor is at least 15% of the receptor binding of human insulin to the insulin receptor. In one aspect, the receptor binding to the insulin receptor is at least 20% of the receptor binding of human insulin to the insulin receptor.

In one aspect, human insulin analogues according to the invention are obtained, wherein the receptor binding to the insulin receptor is increased. In one aspect, human insulin analogues according to the invention are obtained, wherein the receptor binding to the insulin receptor is at least 110% of the receptor binding of human insulin to the insulin receptor. In one aspect, the receptor binding to the insulin receptor is at least 120% of the receptor binding of human insulin to the insulin receptor. In one aspect, the receptor binding to the insulin receptor is at least 130% of the receptor binding of human insulin to the insulin receptor. In one aspect, the receptor binding to the insulin receptor is at least 140% of the receptor binding of human insulin to the insulin receptor. In one aspect, the receptor binding to the insulin receptor is at least 150% of the receptor binding of human insulin to the insulin receptor. In one aspect, the receptor binding to the insulin receptor is at least 160% of the receptor binding of human insulin to the insulin receptor. In one aspect, the receptor binding to the insulin receptor is between 110 and 200% of the receptor binding of human insulin to the insulin receptor. In one aspect, the receptor binding to the insulin receptor is between 120 and 180% of the receptor binding of human insulin to the insulin receptor. In one aspect, the receptor binding to the insulin receptor is between 140 and 180% of the receptor binding of human insulin to the insulin receptor. In one aspect, the receptor binding to the insulin receptor is between 150 and 170% of the receptor binding of human insulin to the insulin receptor.

The receptor binding to the insulin receptor may e.g. be determined as described below:

Insulin Receptor Binding Assay (on Solubilised Insulin Receptor):

The affinity of the human insulin analogue of the invention for the human insulin receptor is determined by a Scintillation Proximity Assay (SPA) (according to Glendorf et al. (2008), *Biochemistry*, 47, 4743-4751). Competition binding experiments were performed in 96-well plates (polystyrene Optiplate-96, PerkinElmer) on an Eppendorf epMotion 5075 robot using solubilized human IR (holoreceptor) semipurified by wheat germ agglutinin purification from baby hamster kidney (BHK) cells, which were stably transfected with the pZem vector containing the human IR-A or IR-B insert. Assays were initiated by making dilution series (eight dilutions, 5-fold each, first dilution 43-fold) of yeast supernatant containing the human insulin analogue and a human insulin standard. A reagent mix consisting of SPA beads (SPA PVT Antibody-Binding Beads, Anti-Mouse Reagent Cat. No. RPNQ0017, GE Healthcare) resuspended in binding buffer, anti-IR monoclonal mouse antibody (83-7), solubilized human IR (hIR-A or hIR-B), and [$^{125}$I]A14Tyr-labelled insulin was added to the dilution series of the appropriate samples.

The final concentration of [$^{125}$I]A14Tyr-labelled insulin was 7.5 pM, and the buffer consisted of 100 mM HEPES (pH 7.8), 100 mM NaCl, 10 mM MgSO4, and 0.025% (v/v) Tween 20. Plates were incubated with gentle shaking for 24 h at room temperature, centrifuged for 2 minutes at 2000 rpm, and counted in a TopCount NXT for 3 min/well. Data from the SPA were analyzed according to the four-parameter logistic model (Vølund, A., (1978), *Biometrics,* 34, 357-365.) and the affinities of the human insulin analogue expressed relative to that of human insulin.

Preparation of Monoclonal mIR Antibodies

Specific antibodies (F12 or 83-7) are produced by monoclonal technique: RBF mice are immunized by injecting 50 µg of purified mIR in FCA subcutaneously followed by two injections with 20 µg of mIR in FIA. High responder mice are boosted intravenously with 25 µg of mIR and the spleens are harvested after 3 days. Spleen cells are fused with the myeloma Fox cell line (Köhler, G & Milstein C. (1976), European J. Immunology, 6:511-19; Taggart R T et al (1983), Science 219:1228-30). Supernatants are screened for antibody production in a mIR specific ELISA. Positive wells are cloned and tested in Western blotting.

Insulin Receptor Binding Assay (on Membrane-Associated Insulin Receptor):

Binding of [$^{125}$I]-human insulin to membrane-associated recombinant human insulin receptor isoform A (hIR-A):

Extraction of membrane-associated insulin receptors: BHK cells (tk-ts13) expressing the human insulin receptor isoform A from a ten-layer cell factory were harvested and homogenised in 25 ml of ice-cold buffer (25 mM HEPES pH 7.4, 2.5 mM CaCl$_2$, 1 mM MgCl$_2$, 250 mg/l bacitracin, 0.1 mM Pefablock (Roche)). The homogenate was layered carefully on 41% sucrose cushions, centrifuged in the ultracentrifuge at 95,000×g for 75 minutes in a Beckman SW28 rotor at 4° C. The plasma membranes were collected from the top of the sucrose cushion, diluted 1:4 with buffer and centrifuged at 40,000×g for 45 min in a Beckman SW28 rotor. The pellets were suspended in buffer (25 mM HEPES pH 7.4, 2.5 mM CaCl$_2$, 1 mM MgCl$_2$, 250 mg/l bacitracin, 0.1 mM Pefablock) and stored at −80° C.

Radioligand binding to membrane-associated insulin receptors was performed in duplicate in 96-well OptiPlates (Perkin Elmer). Membrane protein was incubated for 150 minutes at 25° C. with 50 pM [$^{125}$I-Ty$^{414}$] human insulin in a total volume of 200 ml assay buffer (50 mM HEPES, 150 mM NaCl, 5 mM MgSO$_4$, 0.01% Triton X-100, 0.1% HSA (fatty acid free), Complete™ EDTA-free protease inhibitors), increasing concentrations of human insulin orhuman insulin analogue (typically between 0.01 and 300 nM), and 1 mg of WGA-coated PVT microspheres (GE Healthcare). The assay was terminated by centrifugation of the plate at 2000 RPM for 2 minutes, and bound radioactivity quantified by counting in a Packard TopCount NXT after a delay of 60 minutes.

The binding data were fitted using the four-parameter sigmoidal regression algorithm in GraphPad Prism 5.02 (GraphPad Software, San Diego, Calif.). Results are given as $IC_{50}$ relative to human insulin in %.

In one aspect a human insulin analogue according to the invention is a modified insulin wherein two amino acid residues of human insulin have been substituted by cysteine residues and optionally the amino acid in position B30 has been deleted relative to the amino acid sequence of human insulin.

Modifications in the insulin molecule are denoted stating the chain (A or B), the position, and the one or three letter code for the amino acid residue substituting the native amino acid residue.

Herein terms like "A1", "A2" and "A3" etc. indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end). Using the one letter codes for amino acids, a term like A10C designates that the amino acid in the A10 position is cysteine. Using the three letter codes for amino acids, the corresponding expression is A10Cys.

By "desB30" or "B(1-29)" is meant a natural insulin B chain or an analogue thereof lacking the B30 amino acid and "A(1-21)" means the natural insulin A chain. Thus, e.g., A10C,B1C,desB30 human insulin or alternatively A10Cys, B1Cys,desB30 human insulin is an analogue of human insulin where the amino acid in position 10 in the A chain is substituted with cysteine, the amino acid in position 1 in the B chain is substituted with cysteine, and the amino acid in position 30 in the B chain is deleted.

Herein, the term "amino acid residue" is an amino acid from which, formally, a hydroxy group has been removed from a carboxy group and/or from which, formally, a hydrogen atom has been removed from an amino group.

Examples of insulin analogues are e.g. A10C,B1C human insulin, A10C,B2C human insulin, A10C,B3C human insulin, A10C,B4C human insulin, A10C,B5C human insulin, A10C,B1C,desB30 human insulin, A10C,B2C,desB30 human insulin, A10C,B3C,desB30 human insulin, A10C, B4C,desB30 human insulin and A10C,B5C,desB30 human insulin, B1C, B4C human insulin and B1C, B4C desB30 human insulin.

The production of polypeptides, e.g., insulins, is well known in the art. A human insulin analogue according to the invention may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999. The human insulin analogue may also be produced by a method which comprises culturing a host cell containing a DNA sequence encoding the analogue and capable of expressing the human insulin analogue in a suitable nutrient medium under conditions permitting the expression of the human insulin analogue. Several recombinant methods may be used in the production of human insulin and human insulin analogues. Three non-limiting examples of methods which may be used in the production of insulin in microorganisms such as, e.g., *Escherichia coli* and *Saccharomyces cerevisiae* are, e.g., disclosed in WO2008034881.

Typically, the human insulin analogue is produced by expressing a DNA sequence encoding the human insulin analogue in question or a precursor thereof in a suitable host cell by well known technique as disclosed in e.g. EP 1,246,845 or WO2008034881 both of which patents are herein specifically incorporated by reference.

The human insulin analogue may be expressed with an N-terminal extension as disclosed in EP 1,246,845. After secretion to the culture medium and recovery, the insulin precursor will be subjected to various in vitro procedures to remove the possible N-terminal extension sequence and connecting peptide to give the human insulin analogue. Such methods include enzymatic conversion by means of trypsin or an *Achromobacter lyticus* protease in the presence of an L-threonine ester followed by conversion of the threonine ester of the human insulin analogue into the human insulin analogue by basic or acid hydrolysis as described in U.S. Pat. Nos. 4,343,898 or 4,916,212

Examples of N-terminal extensions of the type suitable in the present invention are disclosed in U.S. Pat. No. 5,395,922 and EP patent No. 765,395 both of which patents are herein specifically incorporated by reference.

The present invention is also related to nucleic acid sequences which code for the claimed insulin analogues. In a further embodiment the present invention is related to vectors containing such nucleic acid sequences and host cells containing such nucleic acid sequences or vectors.

In still a further embodiment, the invention relates to a process for producing a human insulin analogue comprising:
(i) culturing a host cell comprising a nucleic acid sequence encoding an insulin precursor;
(ii) isolating the insulin precursor from the culture medium and
(iii) converting the insulin precursor into a human insulin analogue of the invention by in vitro enzymatic conversion.

In still a further embodiment, the invention relates to a process for producing a human insulin analogue comprising:
(i) culturing a host cell comprising a nucleic acid sequence encoding an insulin precursor;
(ii) isolating the insulin precursor from the culture medium and
(iii) converting the insulin precursor into a human insulin analogue of the invention.

In one embodiment of the present invention the host cell is a yeast host cell and in a further embodiment the yeast host cell is selected from the genus *Saccharomyces*. In a further embodiment the yeast host cell is selected from the species *Saccharomyces cerevisiae*.

In one aspect of the invention a method for stabilizing human insulin is obtained which comprises substituting two or more amino acids of human insulin or desB30 human insulin with cysteine residues, wherein
a. the three disulfide bonds of human insulin are retained and
b. the sites of cysteine substitutions are chosen in such a way that the introduced cysteine residues are placed in the three dimensional structure of the folded insulin analogue to allow for the formation of one or more additional disulfide bonds not present in human insulin, thereby creating a human insulin analogue comprising one or more additional disulfide bonds not present in human insulin.

It is apparent from the description how to obtain an insulin analogue according to the invention. The person skilled in the art thus knows when reading the description how to modify human insulin or desB30 human insulin in such a way that the introduced cysteine residues are placed in the three dimensional structure of the folded insulin analogue to allow for the formation of one or more additional disulfide bonds not present in human insulin in addition to the three disulfide bonds of human insulin.

The number of disulfide bonds in a protein (such as insulin) can be readily determined by accurate intact mass measurements as described, for example in the Examples. The disulfide bonds connectivity can be verified (determined) by standard techniques known in the art, such as peptide mapping. The general strategy for disulfide bond mapping in an insulin peptide includes the following steps: 1) Fragmentation of the non-reduced insulin into disulfide bonded peptides containing, if possible, only a single disulfide bond per peptide. The chosen conditions are also such that rearrangement of disulfide bonds is avoided, 2) Separation of disulfide bonded peptides from each other. 3) Identification of the cysteine residues involved in the individual disulfide bonds.

Human insulin is typically digested by Glu-C protease yielding peptide I containing two disulfide bonds (A6-A11 and A7-B7) and peptide II containing a single disulfide bond (A20-B19). To unambiguously assign the disulfide bonds in peptide I, further fragmentation is necessary. Acid hydrolysis (Ryle at al., 1955 Biochem J. 60, 541-56), manual Edman degradation (Kumazaki T, Ishii, S. 1990 J. Biochem (Tokyo) 17, 414-9). or prolonged digestion with thermolysin (Ota M, Ariyoshi, Y., 1995, Biosci. Biotech. Biochem. 59, 1956-7) were previously employed to hydrolyze CysCys bonds in proteins. An alternative way to assign the disulfide bonds in peptide I is a partial reduction with triscarboxyethyl phosphine (reduction of A7-B7 disulfide bond), alkylation of the reduced cysteine residues followed by complete reduction and cysteine alkylation using a different alkyl group (Yen, T.-Y., Yan, H., Macher, B., 2001 J Mass Spectrom. 37, 15-30).

The strategy for disulfide mapping of insulins containing extra disulfide bonds is in principle the same as outline above for human insulin adjusted for each analogue in such a way that accommodates the new disulfide bond. Determination of insulin structure by NMR or X-ray crystallography is an alternative approach for verifying the disulfide bond connectivity. Conditions for solving NMR and/or X-ray structures of insulin have been described previously and are known in the art.

Pharmaceutical Compositions

Another object of the present invention is to provide a pharmaceutical formulation comprising an insulin analogue according to the present invention which is present in a concentration from 0.1 mg/ml to 500 mg/ml, and wherein said formulation has a pH from 2.0 to 10.0. The formulation may further comprise protease inhibitor(s), a buffer system, preservative(s), tonicity agent(s), chelating agent(s), stabilizers and surfactants. In one embodiment of the invention the pharmaceutical formulation is an aqueous formulation, i.e. formulation comprising water.

In another embodiment the pharmaceutical formulation is a dried formulation (e.g. freeze-dried or spray-dried) ready for use without any prior dissolution.

Pharmaceutical compositions containing an insulin analogue according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

For parenteral administration, an insulin analogue of this invention is formulated analogously with the formulation of known insulins. Furthermore, for parenterally administration, an insulin analogue of this invention is administered analogously with the administration of known insulins and the physicians are familiar with this procedure.

Parenteral administration can be performed by means of a syringe, optionally a penlike syringe. Alternatively, parenteral administration can be performed by means of an infusion pump.

Injectable compositions containing an insulin analogue of this invention can be prepared using the conventional techniques of the pharmaceutical industry which involve dissolving and mixing the ingredients as appropriate to give the desired end product. Thus, according to one procedure, an insulin analogue of this invention is dissolved in an amount of water which is somewhat less than the final volume of the composition to be prepared. An isotonic agent, a preservative and a buffer is added as required and the pH value of the solution is adjusted, if necessary, using an acid, for example, hydrochloric acid, or a base, for example, aqueous sodium hydroxide, as needed. Finally, the volume of the solution is adjusted with water to give the desired concentration of the ingredients.

More precisely, an insulin analogue preparation of this invention, for example a solution or suspension, may be prepared by dissolving a compound of this invention in an aqueous medium at slightly acidic conditions, for example, in a concentration in the range from about 240 to about 2400 nmole/ml. The aqueous medium is made isotonic, for example, with sodium chloride or glycerol. Furthermore, the aqueous medium may contain buffers such as acetate or citrate, preservatives such as m-cresol or phenol and zinc ions, for example, in a concentration of up to about 20 μg of $Zn^{++}$ per unit of insulin activity. The pH value of the solution is adjusted towards neutrality without getting too close to the isoelectric point of the compound of this invention in order to avoid precipitation. The pH value of the final insulin preparation depends upon which compound of this invention is used, the concentration of zinc ions and the concentration of the compound of this invention. The human insulin analogue preparation is made sterile, for example, by sterile filtration.

Formulations intended for oral use may be prepared according to any known method, and such formulations may contain one or more agents selected from the group consisting of sweetening agents, flavouring agents, colouring agents, and preserving agents in order to provide pharmaceutically elegant and palatable preparations. Tablets may contain the active ingredient in a mixture with non-toxic pharmaceutically-acceptable excipients which are suitable for the manufacture of tablets. These excipients may be for example, inert diluents, such as mannitol, maltodextrin, kaolin, calcium carbonate, sodium carbonate, lactose, calcium phosphate or sodium phosphate; granulating and disintegrating agents, for example corn starch; binding agents, for example, starch, gelatine, polymers or acacia; and lubricating agents, for example magnesium stearate, stearic acid or talc. The tablets may be uncoated or they may be coated by known techniques to delay disintegration or release of the therapeutically active polypeptide.

The orally administerable formulations of the present invention may be prepared and administered according to methods well known in pharmaceutical chemistry, see Remington's Pharmaceutical Sciences, $17^{th}$ ed. (A. Osol ed., 1985).

The human insulin analogue preparations of this invention are used similarly to the use of the known insulin preparations.

The amount of a compound of this invention to be administered, the determination of how frequently to administer a compound of this invention, and the election of which compound or compounds of this invention to administer, optionally together with another antidiabetic compound, is decided in consultation with a practitioner who is familiar with the treatment of diabetes.

In one aspect, the human insulin analogue according to the invention is administered orally. In one aspect, the human insulin analogue according to the invention is administered parentally.

In another embodiment, the present invention relates to an insulin analogue according to the invention for use as a medicament.

In one embodiment, an insulin analogue according to the invention is used for the preparation of a medicament for the treatment or prevention of hyperglycemia, type 2 diabetes, impaired glucose tolerance and type 1 diabetes.

In another embodiment, an insulin analogue according to the invention is used as a medicament for delaying or preventing disease progression in type 2 diabetes.

In one embodiment of the invention, the human insulin analogue according to the invention is for use as a medicament for the treatment or prevention of hyperglycemia, type 2 diabetes, impaired glucose tolerance, type 1 diabetes or for delaying or preventing disease progression in type 2 diabetes.

In a further embodiment of the invention, a method for the treatment or prevention of hyperglycemia, type 2 diabetes, impaired glucose tolerance, type 1 diabetes or for delaying or preventing disease progression in type 2 diabetes, the method comprising administering to a patient in need of such treatment an effective amount for such treatment of an insulin analogue according to the invention, is provided.

The term "diabetes" includes type 1 diabetes, type 2 diabetes and other states that cause hyperglycaemia.

The term "treatment" of a disease includes treatment, prevention or alleviation of the disease.

The Following is a List of Aspects Further Describing the Invention:

1. A human insulin analogue having two or more cysteine substitutions where the three disulfide bonds of human insulin are retained, and
the sites of cysteine substitutions are chosen in such a way that the introduced cysteine residues are placed in the three dimensional structure of the folded insulin analogue to allow for the formation of one or more additional disulfide bonds not present in human insulin.

2. A human insulin analogue according to aspect 1, wherein the sites of cysteine substitutions are chosen in such a way that
   (1) the introduced cysteine residues are placed in the three dimensional structure of the folded insulin analogue to allow for the formation of one or more additional disulfide bonds not present in human insulin, and
   (2) the human insulin analogue retains the desired biological activities associated with human insulin.

3. A human insulin analogue according to aspect 1 or 2, wherein the sites of cysteine substitutions are chosen in such a way that
   (1) the introduced cysteine residues are placed in the three dimensional structure of the folded insulin analogue to allow for the formation of one or more additional disulfide bonds not present in human insulin,
   (2) the human insulin analogue retains the desired biological activities associated with human insulin, and
   (3) the human insulin analogue has increased physical stability relative to human insulin and/or parent insulin 4. A human insulin analogue according to any one of the preceding aspects, to the extend possible, wherein the sites of cysteine substitutions are chosen in such a way that
   (1) the introduced cysteine residues are placed in the three dimensional structure of the folded insulin analogue to allow for the formation of one or more additional disulfide bonds not present in human insulin,
   (2) the human insulin analogue retains the desired biological activities associated with human insulin, and
   (3) the human insulin analogue is stabilized against proteolytic degradation.
5. A human insulin analogue according to any one of the preceding aspects, to the extend possible, wherein at least one amino acid residue in a position selected from the group consisting of A9, A10, A11 and A12 of the A-chain is substituted with a cysteine, at least one amino acid residue in a position selected from the group consisting of B1, B2, B3, B4, B5 and B6 of the B-chain is substituted with a cysteine, and optionally the amino acid in position B30 is deleted.
6. A human insulin analogue according to any one of the preceding aspects, to the extend possible, wherein the amino acid residue in position A10 of the A-chain is substituted with a cysteine, the amino acid residue in a position selected from the group consisting of B1, B2, B3 and B4 of the B-chain is substituted with a cysteine, and optionally the amino acid in position B30 is deleted.
7. A human insulin analogue according to any one of the preceding aspects, to the extend possible, wherein the amino acid residue in position A10 of the A-chain is substituted with a cysteine, the amino acid residue in a position selected from the group consisting of B3 and B4 of the B-chain is substituted with a cysteine, and optionally the amino acid in position B30 is deleted.
8. A human insulin analogue according to any one of the preceding aspects, to the extend possible, wherein the amino acid residue in position A10 of the A-chain is substituted with a cysteine, and amino acid in position B3 of the B-chain is substituted with a cysteine, and optionally the amino acid in position B30 is deleted.
9. A human insulin analogue according to any one of the preceding aspects, to the extend possible, wherein the amino acid residue in position A10 of the A-chain is substituted with a cysteine, the amino acid in position B4 of the B-chain is substituted with a cysteine, and optionally the amino acid in position B30 is deleted.
10. A human insulin analogue according to any one of the preceding aspects wherein the amino acid residue in position A21 of the A-chain is substituted with a cysteine, the amino acid residue in a position selected from the group consisting of B25 and B26 of the B-chain is substituted with a cysteine, and optionally the amino acid in position B30 is deleted
11. A human insulin analogue according to any one of the preceding aspects, to the extend possible, wherein one or more additional disulfide bonds are obtained between the A-chain and the B-chain
12. A human insulin analogue according to any one of the preceding aspects, to the extend possible, wherein the receptor binding to the insulin receptor is at least 1% of the receptor binding of human insulin to the insulin receptor.
13. A human insulin analogue according to any one of the preceding aspects, to the extend possible, which has improved physical stability relative to the parent insulin.
14. A human insulin analogue according to any one of the preceding aspects, to the extend possible, wherein the amino acid in position B30 is deleted.
15. A human insulin analogue according to any one of the preceding aspects, to the extend possible, wherein at least one additional disulfide bond is connecting two cysteines in the A-chain or connecting two cysteines in the B-chain.
16. A human insulin analogue according to any one of the preceding aspects, to the extend possible, which has two cysteine substitutions.
17. A human insulin analogue according to any one of the preceding aspects, to the extend possible, which is selected from the group consisting of:
   A10C, B1C, desB30 human insulin
   A10C, B2C, desB30 human insulin
   A10C, B3C, desB30 human insulin
   A10C, B4C, desB30 human insulin
   A21C, B25C, desB30 human insulin
   A21C, B26C, desB30 human insulin
   B1C, B4C, desB30 human insulin
   A10C, B1C human insulin
   A10C, B2C human insulin
   A10C, B3C human insulin
   A10C, B4C human insulin
   A21C, B25C human insulin
   A21C, B26C human insulin, and
   B1C, B4C human insulin
18. A human insulin analogue according to any one of the preceding aspects, to the extend possible, which is selected from the group consisting of:
   A10C, B1C, desB30 human insulin
   A10C, B2C, desB30 human insulin
   A10C, B3C, desB30 human insulin
   A10C, B4C, desB30 human insulin
   B1C, B4C, desB30 human insulin
   A10C, B1C human insulin
   A10C, B2C human insulin
   A10C, B3C human insulin
   A10C, B4C human insulin, and
   B1C, B4C, human insulin
19. A human insulin analogue according to any one of the preceding aspects, to the extend possible, which is selected from the group consisting of:
   A21C, B25C, desB30 human insulin
   A21C, B26C, desB30 human insulin
   A21C, B25C, human insulin, and
   A21C, B26C, human insulin
20. A method for stabilizing human insulin comprising substituting two or more amino acids of human insulin or desB30 human insulin with cysteine residues, wherein
   a. the three disulfide bonds of human insulin are retained and
   b. the sites of cysteine substitutions are chosen in such a way that the introduced cysteine residues are placed in the three dimensional structure of the folded insulin analogue to allow for the formation of one or more additional disulfide bonds not present in human insulin,
   thereby creating a human insulin analogue comprising one or more additional disulfide bonds not present in human insulin.
21. A pharmaceutical composition comprising a biologically active amount of the human insulin analogue according to any one of the aspects 1-19 and a pharmaceutically acceptable carrier.
22. A pharmaceutical composition according to aspect 21 which further comprises a pharmaceutical acceptable carrier and/or excipient, and optionally an adjuvant.
23. A method for the treatment of diabetes mellitus in a subject comprising administering to a subject a human insulin analogue according to any one of the aspects 1-19 or a pharmaceutical composition according to any of the aspects 21-22.

24. A method of reducing the blood glucose level in mammals by administrating to a patient in need of such treatment a therapeutically active dose of a human insulin analogue according to any one of the aspects 1-19 or a pharmaceutical composition according to any of the aspects 21-22.

25. Method according to aspect 21 or 22 being an oral administration.

26. Method according to aspect 21 or 22 being parenteral administration.

27. Method according to aspect 21 or 22 being intratracheal administration.

28. A human insulin analogue according to any one of the aspects 1-19 for use as a pharmaceutical in the treatment or prevention of hyperglycemia, type 2 diabetes, impaired glucose tolerance and type 1 diabetes.

29. A human insulin analogue according to any one of the aspects 1-19 for use as a pharmaceutical in delaying or preventing disease progression in type 2 diabetes.

30. A nucleic acid sequence encoding a human insulin analogue according to any one of the aspects 1-19, a derivative thereof, a partial sequence thereof, a degenerated sequence thereof or a sequence which hybridises thereto under stringent conditions.

31. A nucleic acid sequence encoding a precursor of a human insulin analogue according to any one of the aspects 1-19, a derivative thereof, a partial sequence thereof, a degenerated sequence thereof or a sequence which hybridises thereto under stringent conditions.

32. An expression vector comprising a nucleic acid sequence according to aspect 30 or 31.

33. A host cell comprising an expression vector according to aspect 32.

34. A method of producing a human insulin analogue comprising the step of cultivating the host cell of aspect 33.

35. A method of preparing a human insulin analogue according to any one of the aspects 1-19 wherein the cysteine substitution of amino acids is carried out by site-directed mutagenesis.

36. A process for preparing a pharmaceutical composition according to any one of the aspects 21-22 comprising mixing a human insulin analogue according to any one of the aspects 1-19 with pharmaceutically acceptable substances and/or excipients.

37. A pharmaceutical composition obtainable by the process according to aspect 36.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

The following examples are offered by way of illustration, not by limitation.

The abbreviations used herein are the following: γGlu is gamma L-glutamyl, HCl is hydrochloric acid, MeCN is acetonitrile, OEG is [2-(2-aminoethoxy)ethoxy]ethylcarbonyl, RPC is reverse phase chromatography, RT is room temperature, TFA is trifluoroacetic acid, The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

Construction of vectors, yeast expression, processing and purification of insulin analogues can be done using the standard techniques readily recognised by those skilled in the art. One non-limiting example of preparation of insulin analogues (general procedure (A)) was described previously (Glendorf, T., Sørensen, A. R., Nishimura, E., Pettersson, I. and Kjeldsen, T. *Importance of the Solvent-Exposed Residues of the Insulin B Chain α-Helix for Receptor Binding. Biochemistry* 2008, 47, 4743-4751). Briefly, mutations are introduced to insulin coding vectors using overlap extension PCR. Insulin analogues are expressed as proinsulin-like fusion proteins, with an Ala-Ala-Lys mini C-peptide in *Saccharomyces cerevisiae* strain MT663. The single-chain precursors are enzymatically converted into two-chain desB30 analogues using *A. lyticus* endoprotease. Full conversion to the two-chain desB30 analogue is verified by MALDI-TOF MS, and its purity is measured by RP-HPLC at both acidic and neutral pH.

Purification:

The compounds of the invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question et cetera, these modifications can readily be recognised and made by a person skilled in the art.

Purification of the human insulin analogues is performed in one and/or two steps:

1) acidified and clarified culture supernatant are captured by adsorption to a cation exchange column and/or 2) insulin analogues are purified by preparative reverse phase high pressure liquid chromatography on a C18 silica column with for example an ethanol/water gradient in phosphate buffer at pH 3.

After neutral HPLC or anion exchange chromatography, the compounds are desalted, e.g. by size exclusion chromatography, precipitated at isoelectric pH, or desalted by acidic HPLC.

After acidic HPLC or desalting, the compounds are isolated by lyophilisation of the pure fractions.

Typical Purification Procedures:

The HPLC system is a Gilson system consisting of the following: Model 215 Liquid handler, Model 322-H2 Pump and a Model 155 UV Detector. Detection is typically at 210 nm and 280 nm.

The Äkta Purifier FPLC system (Amersham Biosciences) consists of the following: Model P-900 Pump, Model UV-900 UV detector, Model pH/C-900 pH and conductivity detector, Model Frac-950 Fraction collector. UV detection is typically at 214 nm, 254 nm and 276 nm.

Acidic HPLC:
Column: Macherey-Nagel SP 250/21 Nucleusil 300-7 C4
Flow: 8 ml/min
Buffer A: 0.1% TFA in acetonitrile
Buffer B: 0.1% TFA in water.
Gradient: 0.0-5.0 min: 10% A
5.00-30.0 min: 10% A to 90% A
30.0-35.0 min: 90% A
35.0-40.0 min: 100% A
Neutral HPLC:
Column: Phenomenex, Jupiter, C4 5 µm 250×10.00 mm, 300 Å
Flow: 6 ml/min
Buffer A: 5 mM TRIS, 7.5 mM $(NH_4)_2SO_4$, pH=7.3, 20% $CH_3CN$
Buffer B: 60% $CH_3CN$, 40% water
Gradient: 0-5 min: 10% B
5-35 min: 10-60% B
35-39 min: 60% B
39-40 min: 70% B
40-43.5 min: 70% B
Anion Exchange Chromatography:
Column: RessourceQ, 1 ml
Flow: 6 ml/min
Buffer A: 0.09% $NH_4HCO_3$, 0.25% $NH_4OAc$, 42.5% ethanol pH 8.4
Buffer B: 0.09% $NH_4HCO_3$, 2.5% $NH_4OAc$, 42.5% ethanol pH 8.4
Gradient: 100% A to 100% B during 30 column volumes
Desalting:
Column: HiPrep 26/10
Flow: 10 ml/min, 6 column volumes
Buffer: 10 mM $NH_4HCO_3$ Preparation of A10C, B3C Human Insulin:

0.23 g L-Threonine methyl ester was dissolved in water (1 mL) and added N-methylpyrrolonine-2-one (NMP) and 200 mg A10C, B3C, desB30 Human insulin was added. The resulting pH (8.2) was adjusted to pH 6.6 with aqueous acetic acid. ALP III Sepharose 4 fast flow (Novo Nordisk) was added to the mixture and the mixture was gently stirred at room temperature for 3 hours. pH was adjusted to 1.5 with hydrochloric acid and the mixture was filtered. The filtrate was added acetonitrile (2 mL) and pH was adjusted to 7.5 with 1 N sodium hydroxide. The A10C, B3C B30T methylester human insulin was purified by HPLC using a Phenomenex, Gemini, 5µ, C18, 110 Å, 250×30 cm column and the following eluents and gradients:

Flow: 20 ml/min
Eluents: A: 20% CH3CN 10 mM TRIS+15 mM (NH4)SO4 pH=7.3
B: 80% CH3CN, 20% water
Gradient: 0-7.5 min: 10% B,
7.5-47.5 min: 10% B to 60% B
47.5-47.5 min: 60% B
47.5-48 min: 60% B to 100% B
48-50 min: 100% B
50-53 min: 10% B Pure fractions were pooled and pH was adjusted to 1.5 with 1N hydrochloric acid and desalted on a Phenomenex, Gemini, 5µ, C18, 110 Å, 250×30 cm column using the following eluents and gradients:

Flow: 20 ml/min'
Eluents A: 0.1% Trifluoroacetic acid in water
B: 0.1% Trifluoroacetic acid in acetonitrile
Gradient: 0-7.5 min: 0% B,
7.5-27.5 min: 0% B to 60% B,
27.5-32.5 min: 60% B
32.5-38 min: 60% B to 100% B
38-40 min: 100% B
40-43 min: 10% B Insulin containing fractions were pooled and lyophilised to afford 14 mg of A10C, B3C B30T methylester human insulin This was dissolved in 1.4 mL ice cold 0.1 N sodium hydroxide and was allowed to stand for 1 hour and at room temperature for 30 minutes. Ph was then adjusted to 2.5 with 1N hydrochloric acid and the insulin was purifies by HPLC using a Phenomenex, Gemini, 5µ, C18, 110 Å, 250×30 cm column and using the following eluents and gradients:

Flow: 20 ml/min'
Eluents: A: 0.1% Trifluoroacetic acid in water TFA iCH3CN
B: 0.1% Trifluoroacetic acid in acetonitrile
Gradient: 0-7.5 min: 25% B,
7.5-47.5 min: 25% B to 55% B,
47.5-52.5 min: 55% B
52.5-57.5 min: 55% B to 100% B
57.5-60 min: 100% B Lyophilisation of pure fractions afforded 4.5 mg A10C, B3C Human insulin MS (electrospray) m/4: m/z=1447.46. Calcd: 1447.17

Preparation of A10C, B4C Human Insulin:

This analogue was prepared analogously with the B3C analogue above starting from A10C, B4C, desB30 human insulin and L-Threonine methyl ester. The product obtained after alkaline hydrolysis (6 mg) was the desired A10C, B4C Human insulin.

MS (electrospray) m/4: m/z=1444.02. Calcd: 1443.66

Alternatively, these analogues may be prepared using the procedure published by J. Markussen: Human Insulin by Tryptic Transpeptidation of Porcine Insulin and Biosynthetic P Method 1. Insulin analogues are analyzed by an Alliance HPLC system (Waters, Milford, Mass.) using a C18 reversed-phase HPLC column. Insulin analogues separation is achieved employing a linear gradient of acetonitrile in phosphate/sulphate buffer.

Column: ODDMS 120 Å, 5 μm, YMC 4×125 mm, FeF Chemicals

Flow: 1 ml/min

Buffer A:

Buffer B: 43.8% (w/w) acetonitrile in water

Gradient: 20% B to 50% B in 20 min, 50% B to 80% B in 5 min

Temperature: 50° C.

Method 2; LC-MS instrumentation consists of Acquity UPLC system (Waters, Milford, Mass.) and Synapt G2 mass spectrometer (Waters, Milford, Mass.). Insulin analogues are applied to a C18 reversed-phase HPLC column and analyzed using a linear gradient of acetonitrile in 0.05% trifluoroacetic acid. The flow from HPLC is applied directly to the electrospray interface of the Synapt G2 operating in the positive MS only mode with 2500 V capillary potential, 110° C. source temperature, 250° C. desolvation temperature and cone gas flow ($N_2$) of 50 L/h. MS spectra from m/z=100 to m/z=3000 are acquired twice per second. Instrument is calibrated by a standard mixture of NaI prior to analyses and lock spray of leucine enkephalin is applied during LC-MS analyses. Intact insulin masses are reconstructed by BioPharmaLynx 1.2 (Waters, Milford, Mass.) using MaxEnt3 algorithm. Orbitrap XL mass spectrometer (Thermo Fisher) can be used instead of Synapt G2. Orbitrap instrument is operated in the positive MS mode with source voltage of 4 kV, source current of 100 μA, sheath gas flow of 40, auxiliary gas flow of 10, sweep gas flow of 5, capillary voltage of 20 V. All MS parameters are adjusted during tuning of the instruments for optimal performance and may deviate slightly from those given above. Mass accuracy obtained by this method is better than 10 ppm.

Column: Acquity BEH C18 1×150 mm, 1.7 μm (Waters)

Flow: 0.1 ml/min

Buffer A: 0.02% (v/v) or 0.05% (v/v) TFA

Buffer B: 0.02% (v/v) or 0.04% (v/v) TFA in acetonitrile

Gradient: 5% B for 2 min; 5% B to 50% B in 12 min, 50% B to 90% B in 1 min

UV Detection: 215 nm

Method 3; Supernatants from the yeast cultures containing insulin analogues are acidified using 10% TFA solution and spotted onto PAC384 MALDI plate (Bruker Daltonics, Bremen, Germany) containing HCCA matrix spots. Each spot is washed twice using ammonium phosphate/0.1% TFA finishing solution. Samples are analyzed using an Autoflex Tof/Tof MALDI mass spectrometer (Bruker) operated in a linear positive mode and calibrated using a home-made mixture of insulin analogs. This method allows for average mass resolution in the range of intact insulin analogs (4000-8000 Da). Precision of this method is ±3 Da.

The results given in each of the following examples represent an average from multiple measurements and/or in some cases single measurements. In some instances additional measurements have been conducted since filing the first priority application and this could lead to adjustments of the average values, explaining slightly different values in different versions of the application.

Example 1

General Procedure (A)

A10C, 131C, desB30 Human Insulin
  Retention time in HPLC method 1: RT=15.5 min
  Method 2: RT=10.6 min; Theoretic Mass=5646.44 Da; Measured Mass=5646.46 Da Example 2

General Procedure (A)

A10C, B2C, desB30 Human Insulin
  HPLC method 1: RT=14.3 min
  Method 2: RT=10.3 min; Theoretic Mass=5694.44 Da; Measured Mass=5694.46 Da Example 3

General Procedure (A)

A10C, B3C, desB30 Human Insulin
  HPLC method 1: RT=13.3 min
  Method 2: RT=10.1 min; Theoretic Mass=5679.47 Da; Measured Mass=5679.48 Da Example 4

General Procedure (A)

A10C, B4C, desB30 Human Insulin
  HPLC method 1: RT=13.3 min
  Method 2: RT=10.1 min; Theoretic Mass=5665.45 Da; Measured Mass=5665.46 Da Example 5

General Procedure (A)

A10C, B3C Human Insulin
  Method 2: RT=10 min; Theoretic Mass=5780.51 Da; Measured Mass=5780.52 Da Example 6

General Procedure (A)

A10C, B4C Human Insulin
  Method 2: RT=10 min; Theoretic Mass=5766.5 Da; Measured Mass=5766.48 Da Example 7

General Procedure (A)

B1C, B4C, desB30 Human Insulin
  HPLC method 1: RT=20.5 min
  Average mass method 3: Expected=5635.5 Da, Measured=5636.5 Da

Example 8

General Procedure (A)

A21C, B25C, desB30 Human Insulin
  HPLC method 1: RT=17.1 min
  Average mass method 3: Expected=5649.6 Da, Measured=5652.4 Da

Example 9

General Procedure (A)

A21C, B26C, desB30 Human Insulin
  HPLC method 1: RT=15.5 min
  Method 2: RT=11.1 min; Theoretic Mass=5629.49 Da; Measured Mass=5629.49 Da

Example b 10

Insulin Receptor Affinity of Selected Insulin Analogues of the Invention

Insulin Receptor Binding Assay (on Solubilised Insulin Receptor)

The affinity of the human insulin analogue of the invention for the human insulin receptor was determined by a Scintillation Proximity Assay (SPA) (according to Glendorf et al. (2008), Biochemistry, 47, 4743-4751). Competition binding experiments were performed in 96-well plates (polystyrene Optiplate-96, PerkinElmer) on an Eppendorf epMotion 5075 robot using solubilized human IR (holoreceptor) semipurified by wheat germ agglutinin purification from baby hamster kidney (BHK) cells, which were stably transfected with the pZem vector containing the human IR-A or IR-B insert. Assays were initiated by making dilution series (eight dilutions, 5-fold each, first dilution 43-fold) of yeast supernatant containing the human insulin analogue and a human insulin standard. A reagent mix consisting of SPA beads (SPA PVT Antibody-Binding Beads, Anti-Mouse Reagent Cat. No. RPNQ0017, GE Healthcare) resuspended in binding buffer, anti-IR monoclonal mouse antibody (83-7), solubilized human IR (hIR-A or hIR-B), and $[^{125}I]$A14Tyr-labelled insulin was added to the dilution series of the appropriate samples. The final concentration of $[^{125}I]$A14Tyr-labelled insulin was 7.5 pM, and the buffer consisted of 100 mM HEPES (pH 7.8), 100 mM NaCl, 10 mM MgSO4, and 0.025% (v/v) Tween 20. Plates were incubated with gentle shaking for 24 h at room temperature, centrifuged for 2 minutes at 2000 rpm, and counted in a TopCount NXT for 3 min/well. Data from the SPA were analyzed according to the four-parameter logistic model (Vølund, A., (1978), Biometrics, 34, 357-365.) and the affinities of the human insulin analogue expressed relative to that of human insulin.

Preparation of Monoclonal mIR Antibodies
  Specific antibodies (F12 or 83-7) were produced by monoclonal technique: RBF mice were immunized by injecting 50 µg of purified mIR in FCA subcutaneously followed by two injections with 20 µg of mIR in FIA. High responder mice were boosted intravenously with 25 µg of mIR and the spleens were harvested after 3 days. Spleen cells were fused with the myeloma Fox cell line (Köhler, G & Milstein C. (1976), European J. Immunology, 6:511-19; Taggart R T et al (1983), Science 219:1228-30). Supernatants were screened for antibody production in a mIR specific ELISA. Positive wells were cloned and tested in Western blotting.

Insulin Receptor Affinities of Selected Insulins of the Invention:

| Example # | Relative Affinity to Human Insulin Receptor A |
|---|---|
| 1 | 56.9 |
| 2 | 164.9 |
| 3 | 51.3 |
| 4 | 162.4 |
| 5 | 23.7 |
| 6 | 161.4 |
| 7 | 80.0 |
| 8 | 1.0 |
| 9 | 0.5 |

Example 11

Degradation of Insulin Analogues Using Duodenum Lumen Enzymes

Degradation of insulin analogues using duodenum lumen enzymes (prepared by filtration of duodenum lumen content) from SPD rats. The assay was performed by a robot in a 96 well plate (2 ml) with 16 wells available for insulin analogues and standards. Insulin analogues ~15 µM were incubated with duodenum enzymes in 100 mM Hepes, pH=7.4 at 37° C., samples were taken after 1, 15, 30, 60, 120 and 240 min and reaction quenched by addition of TFA. Concentrations of intact human insulin analogues at each point were determined by RP-HPLC. Degradation half time was determined by exponential fitting of the data (for example, single exponential decay, 2 parameters, Sigma Plot version 11, Systat Software) and normalized to half time determined for the reference insulins and/or human insulin in each assay. The result is given as the degradation half time for the human insulin analogue in rat duodenum divided by the degradation half time of the reference insulin from the same experiment (relative degradation rate).

| Example # | Duodenum Degradation Relative Stability vs. Human Insulin |
|---|---|
| 1 | 0.9 |
| 2 | 1.1 |
| 3 | 2.2 |
| 4 | 3.5 |
| 5 | 1.9 |
| 6 | 2.8 |
| 8 | 6.6 |
| 9 | 5.4 |

Example 12

Melting Point Determinations

Differential Scanning Calorimetry (DSC).
  Data collection was performed using a VP-DSC differential scanning microcalorimeter (MicroCal, LLC, Northampton, Mass.). All protein scans (~200 µM insulin analogs) were performed with 2 mM phosphate buffer in the reference cell from 10° C. to 110° C. at a scan rate of 1° C./min and an excess pressure of 0.21 MPa. All samples and references were degassed immediately before use. A buffer-buffer reference scan was subtracted from each sample scan prior to concentration normalization.

Figure 1:
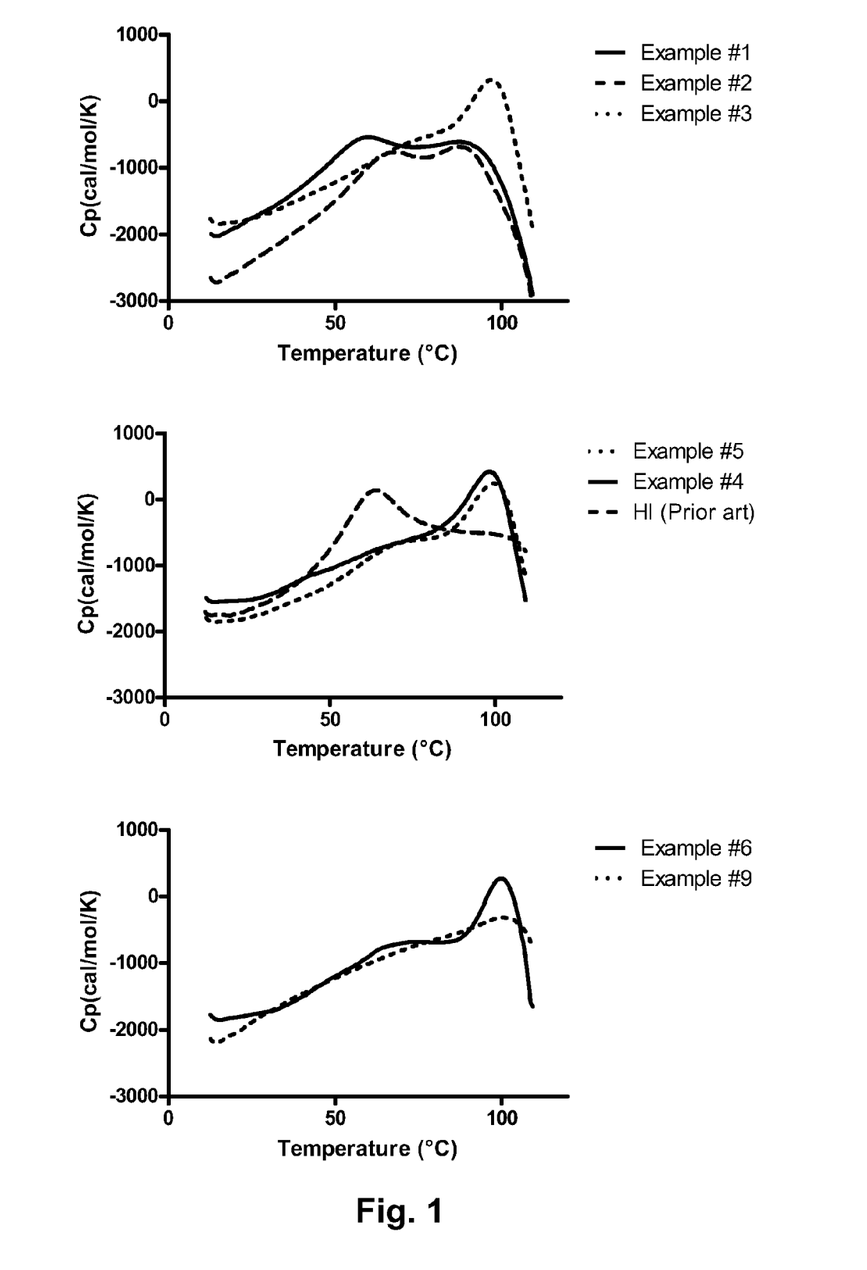
FIG. 1. Differential Scanning calorimetry (DSC) comparison of human insulin (prior art) and the human insulin analogues described in examples 1-3 (panel A), human insulin (prior art) and examples 4, 5 (panel B), and examples 6 and 9 (panel C).

DSC results are shown in FIG. 1

Example 13

Measurement of Tendencies of Fibrillation

General Procedure for Thioflavin T (ThT) Fibrillation Assay:
Principle:

Low physical stability of a peptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore the application of a small molecule indicator probe is much preferred. Thioflavin T (ThT) is such a probe and has a distinct fluorescence signature when binding to fibrils (Naiki et al. Anal. Biochem. 177, 244-249, 1989; Le-Vine, Methods Enzymol. 309, 274-284, 1999). The time course for fibril formation can be described by a sigmoidal curve with the following expression (Nielsen at al. Biochemistry 40, 6036-6046, 2001):

$$F = f_i + m_i t + \frac{f_f + m_f t}{1 + e^{-[(t-t_0)/\tau]}} \quad \text{Eq. (1)}$$

Here, F is the ThT fluorescence at the time t. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$.

Formation of a partially folded intermediate of the peptide is suggested as a general initiating mechanism for fibrillation. Few of those intermediates nucleate to form a template onto which further intermediates may assemble and the fibrillation proceeds. The lag-time corresponds to the interval in which the critical mass of nucleus is built up and the apparent rate constant is the rate with which the fibril itself is formed.

Sample Preparation:

Samples were prepared freshly before each assay. Each analogue was dissolved in 7 mM sodium phosphate, pH=7.4. Thioflavin T was added to the samples from a stock solution in water to a final concentration of 1 µM. Sample aliquots of 200 µl were placed in a 96 well microtiter plate (Packard Optiplate™-96, white polystyrene). Usually four replica of each sample (corresponding to one test condition) were placed in one column of wells. The plate was sealed with Scotch Pad (Qiagen).

Incubation and Fluorescence Measurements:

Incubation at given temperature, shaking and measurements of the ThT fluorescence emission were done in either a Fluoroskan Ascent FL or Varioskan fluorescence plate reader (thermo Labsystems). The temperature was adjusted to 37° C. The orbital shaking was adjusted to 960 rpm with an amplitude of 1 mm in all the presented data. Fluorescence measurements were done using excitation through a 444 nm filter and measurement of emission through a 485 nm filter.

Each run was initiated by incubating the plate at the assay temperature for 10 min. The plate was measured every 20 minutes for typically 45 hours. Between each measurement, the plate was shaken and heated as described above.

Data Handling:

The measurement data points were saved in Microsoft Excel format for further processing and curve drawing and fitting was performed using Graph Pad Prism. The background emission from ThT in the absence of fibrils was negligible. The data points are typically a mean of four samples. Only data obtained in the same experiment (i.e. samples on the same plate) are presented in the same graph ensuring a relative measure of fibrillation between the individual samples of one assay rather then comparison between different assays.

The data set may be fitted to Eq. (1). However since the full sigmoidal curves are not usually achieved during the measurement time, the degree of fibrillation is expressed as ThT fluorescence at various time points calculated as the mean of the four samples and shown with the standard deviation Typical lag time for human insulin (prior art) is <2 h. All compounds described in this invention that were tested in this assay showed no fibrillation in the 45 h duration of the experiment.

| Example # | 0 h | 2 h | 20 h | 45 h |
|---|---|---|---|---|
| human insulin (prior art) | 24 ± 0 | 1508 ± 133 | 2115 ± 48 | 2049 ± 48 |
| 1 | 30.2 ± 0.7 | 21.5 ± 0.5 | 22.8 ± 0.5 | 26.1 ± 0.6 |
| 2 | 29 ± 0.5 | 19.1 ± 1.4 | 18.9 ± 3.1 | 18.3 ± 3.1 |
| 3 | 43.2 ± 0.6 | 28.3 ± 0.8 | 25.7 ± 1.9 | 23.5 ± 1.9 |
| 4 | 42 ± 2 | 35 ± 0 | 33 ± 0 | 31 ± 1 |

Figure 2:
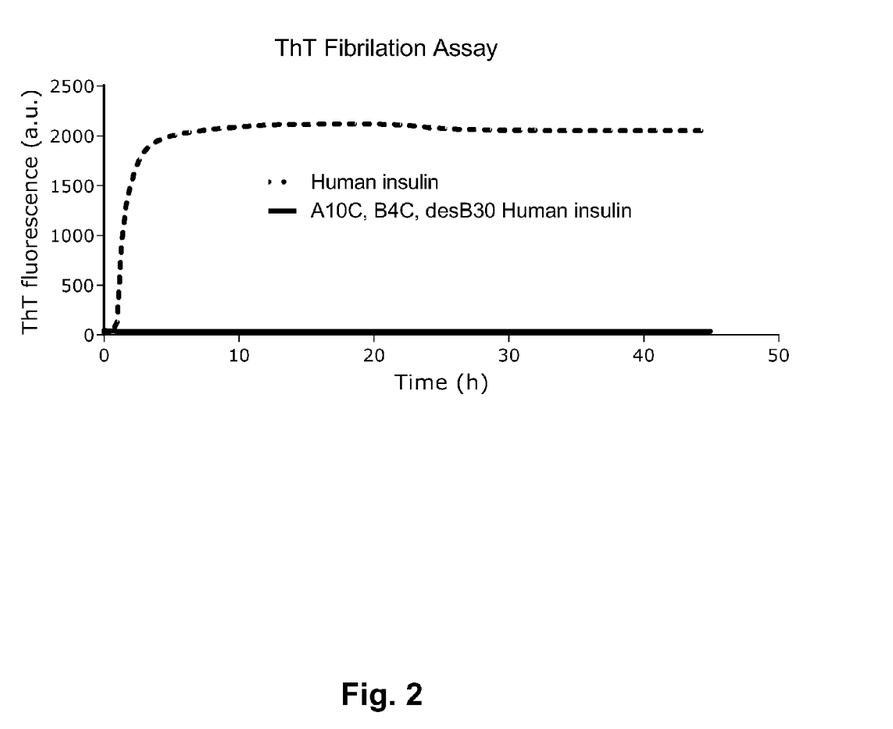
FIG. 2. ThT fibrilation assay comparison of human insulin (prior art) and the human insulin analogue described in example 4 of this invention. Human insulin fibrillation was readily detected with a lag time of <2 h, the human insulin analogue described in example 4 of this invention did not fibrillate within the 45 h duration of the experiment. These results are consistent with superior physical stability of the insulins of the invention.

Fibrillation propensities are shown in FIG. 2

Example 14

Hydrophobicity of the Human Insulin Analogues of the Invention

The hydrophobicity of an insulin analogue is found by reverse phase HPLC run under isocratic conditions. The elution time of the human insulin analogue is compared to that of human insulin (herein designated HI) or another analogue with a known hydrophibicity under the same conditions. The hydrophobicity, k'rel, is calculated as: $k'rel_{deriv} = ((t_{deriv} - t_0)/(t_{re} - t_0))*k'rel_{ref}$. Using HI as reference: $k'rel_{ref} = k'rel_{HI} = 1$. The void time of the HPLC system, $t_0$, is determined by injecting 5 µl of 0.1 mM $NaNO_3$. Running conditions:

Column: Lichrosorb RP-C18, 5 µm, 4×250 mm
Buffer A: 0.1 M natrium phosphate pH 7.3, 10 vol % $CH_3CN$
Buffer B: 50 vol % $CH_3CN$
Injection volume: 5 µl
Run time: max 60 minutes After running an initial gradient, the isocratic level for running the derivative and reference (for example HI) is chosen, and the elution times of the analogue and reference under isocratic conditions are used in the above equation to calculate $k'rel_{deriv}$.

Example 15

Rat Pharmacokinetics, Intravenous Rat PK

Anaesthetized rats were dosed intravenously (i.v.) with insulin analogues at various doses and plasma concentrations of the employed compounds were measured using immunoassays or mass spectrometry at specified intervals for 4 hours or more post-dose. Pharmacokinetic parameters were subsequently calculated using WinNonLin Professional (Pharsight Inc., Mountain View, Calif., USA).

Non-fasted male Wistar rats (Taconic) weighing approximately 200 gram were used.

Body weight was measured and rats were subsequently anaesthetized with Hypnorm/Dormicum (each compound is separately diluted 1:1 in sterile water and then mixed; prepared freshly on the experimental day). Anaesthesia was initiated by 2 ml/kg Hypnorm/Doricum mixture sc followed by two maintenance doses of 1 ml/kg sc at 30 min intervals and two maintenance doses of 1 ml/kg sc with 45 min intervals. If required in order to keep the rats lightly anaesthetised throughout a further dose(s) 1-2 ml/kg sc was supplied. Weighing and initial anaesthesia was performed in the rat holding room in order to avoid stressing the animals by moving them from one room to another.

Example 16

Blood Glucose Lowering Effect, Intravenous Rat PK

Male, fed Wistar rats (250-300 g) were anesthetized using Hypnorm-Dormicum (0.081 mg/ml fentanyl citrate and 1.25 mg/ml Midazolam) 2 ml/kg as a priming dose (time=−35 min) and additional 1 ml/kg to time=−5 min prior to test substance dosing, and then 1 ml/kg every 45 minutes (4 times).

The rats were allocated into 5 groups, 4-6 rats in each group being administrated human insulin and insulin analogues were administered in two doses (1.6 nmol/kg and 3.6 nmol/kg). The animals were dosed with an intravenous injection in a tail vein (1 ml/kg) of either vehicle (5 mM phosphate buffer, 140 mM NaCl, 70 ppm polysorbate 20, pH 7.4) or insulins. Blood samples for the determination of whole blood glucose concentration were collected in heparinized 10 µl glass tubes by puncture of the capillary vessels in the tail tip to timepoints before dosing and after dosing. The blood glucose concentrations were measured after dilution in analysis buffer (500 µl) by the immobilized glucose oxidase method using a Biosen autoanalyzer (EKF Diagnostic, Germany).

Figure 3:
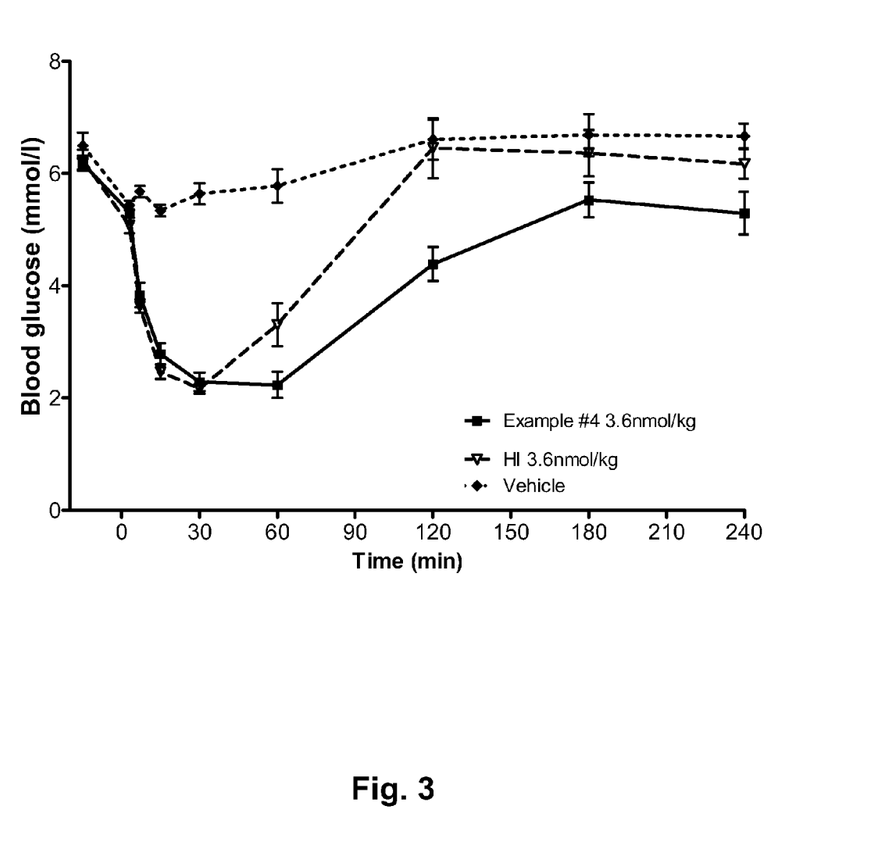
FIG. 3. Blood glucose profiles following i.v administration of human insulin (prior art) and the human insulin analogue described in example 4 of this invention. The two compounds were administrated 3.6 nmol/kg doses (mean values±SEM).

PD profiles are shown in FIG. 3

Example 17

Rat Pharmacokinetics, Rat PK Following Intraintestinal Injection

Anaesthetized rats are dosed intraintestinally (into jejunum) with insulin analogues. Plasma concentrations of the employed compounds as well as changes in blood glucose are measured at specified intervals for 4 hours or more post-dosing. Pharmacokinetic parameters are subsequently calculated using WinNonLin Professional (Pharsight Inc., Mountain View, Calif., USA).

Male Sprague-Dawley rats (Taconic), weighing 250-300 g, fasted for ~18 h are anesthetized using Hypnorm-Dormicum s.c. (0.079 mg/ml fentanyl citrate, 2.5 mg/ml fluanisone and 1.25 mg/ml midazolam) 2 ml/kg as a priming dose (to time-point −60 min prior to test substance dosing), 1 ml/kg after 20 min followed by 1 ml/kg every 40 min.

The insulins to be tested in the intraintestinal injection model are formulated according to the following composition (in weight %):

| | |
|---|---|
| 45% Propylene glycol | (Merck) |
| 33% Capmul MCM C10 | (Abitec) |
| 11% Poloxamer 407 | (BASF) |
| 11% Polyethyleneglycol 3350 Ultra | (Fluka) |

The amount of added insulin is subtracted equally from Capmul MCM C10, Poloxamer 407 and PEG 3350 and not from propylene glycol in order to keep the amount of propylene glycol independent of the drug load constant at 45%.

The anesthetized rat is placed on a homeothermic blanket stabilized at 37° C. A 20 cm polyethylene catheter mounted a 1-ml syringe is filled with insulin formulation or vehicle. A 4-5 cm midline incision is made in the abdominal wall. The catheter is gently inserted into mid-jejunum ~50 cm from the caecum by penetration of the intestinal wall. If intestinal content is present, the application site is moved ±10 cm. The catheter tip is placed approx. 2 cm inside the lumen of the intestinal segment and fixed without the use of ligatures. The intestines are carefully replaced in the abdominal cavity and the abdominal wall and skin are closed with autoclips in each layer. At time 0, the rats are dosed via the catheter, 0.4 ml/kg of test compound or vehicle.

Blood samples for the determination of whole blood glucose concentrations are collected in heparinised 10 µl capillary tubes by puncture of the capillary vessels in the tail tip. Blood glucose concentrations are measured after dilution in 500 µl analysis buffer by the glucose oxidase method using a Biosen autoanalyzer (EKF Diagnostic Gmbh, Germany). Mean blood glucose concentration courses (mean±SEM) are made for each compound.

Samples are collected for determination of the plasma insulin concentration. 100 µl blood samples are drawn into chilled tubes containing EDTA. The samples are kept on ice until centrifuged (7000 rpm, 4° C., 5 min), plasma is pipetted into Micronic tubes and then frozen at 20° C. until assay. Plasma concentrations of the human insulin analogues are measured in a immunoassay which is considered appropriate or validated for the individual derivative.

Blood samples are drawn at t=−10 (for blood glucose only), at t=−1 (just before dosing) and at specified intervals for 4 hours or more post-dosing.

Example 18

Potency of Insulin Analogues of this Invention Relative to Human Insulin, Intravenous Steady-State Clamp Sprague Dawley male rats weighing 238-383 g on the experimental day are used for the clamp experiment. The rats have free access to feed under controlled ambient conditions and are fasted overnight (from 3 µm) prior to the clamp experiment.

Experimental Protocol:

The rats are acclimatized in the animal facilities for at least 1 week prior to the surgical procedure. Approximately 1 week prior to the clamp experiment, Tygon catheters are inserted under halothane anaesthesia into the jugular vein (for infusion) and the carotid artery (for blood sampling) and exteriorised and fixed on the back of the neck. The rats are given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) is administered during anaesthesia and Rimadyl (1.5 mg/kg, s.c.) is administered after full recovery from the anaesthesia (2-3 h) and again once daily for 2 days.

At 7 am on the experimental day overnight fasted (from 3 µm the previous day) rats are weighed and connected to the sampling syringes and infusion system (Harvard 22 Basic pumps, Harvard, and Perfectum Hypodermic glass syringe, Aldrich) and then placed into individual clamp cages where they rest for ca. 45 min before start of experiment. The rats are able to move freely on their usual bedding during the entire experiment and have free access to drinking water. After a 30 min basal period during which plasma glucose levels were measured at 10 min intervals, the human insulin analogue to be tested and human insulin (one dose level per rat, n=6-7 per dose level) are infused (i.v.) at a constant rate for 300 min. Optionally a priming bolus infusion of the human insulin analogue to be tested is administered in order to reach immediate steady state levels in plasma. The dose of the priming bolus infusion can be calculated based on clearance data obtained from i.v. bolus pharmacokinetics by a pharmacokinetician skilled in the art. Plasma glucose levels are measured at 10 min intervals throughout and infusion of 20% aqueous glucose is adjusted accordingly in order to maintain euglyceamia. Samples of re-suspended erythrocytes are pooled from each rat and returned in about ½ ml volumes via the carotid catheter.

On each experimental day, samples of the solutions of the individual insulin analogues to be tested and the human insulin solution are taken before and at the end of the clamp experiments and the concentrations of the peptides are confirmed by HPLC. Plasma concentrations of rat insulin and C-peptide as well as of the human insulin analogue to be tested and human insulin are measured at relevant time points before and at the end of the studies. Rats are killed at the end of experiment using a pentobarbital overdose.

Example 19

Lipogenesis in Rat Adipocytes

As a measure of in vitro potency of the insulins of the invention, lipogenesis can be used.

Primary rat adipocytes are isolated from the epididymale fat pads and incubated with 3H-glucose in buffer containing e.g. 1% fat free HSA and either standard (human insulin, HI) or insulin of the invention. The labelled glucose is converted into extractable lipids in a dose dependent way, resulting in full dose response curves. The result is expressed as relative potency (%) with 95% confidence limits of insulin of the invention compared to standard (HI).

The invention claimed is:

1. An analogue of human insulin where the analogue contains one additional disulfide bond not present in human insulin and wherein
   i) the three disulfide bonds of human insulin are retained,
   ii) the amino acid at position A10 of the A chain of human insulin is substituted with a cysteine,
   iii) one amino acid selected from the group consisting of positions B1, B2, B3 and B4 of the B chain of human insulin is substituted with a cysteine, and
   iv) optionally the amino acid at position B30 of human insulin is deleted.

2. An analogue of human insulin according to claim 1, wherein one amino acid residue in a position selected from the group consisting of B3 and B4 of the B-chain is substituted with a cysteine.

3. An analogue of human insulin according to claim 1, which is selected from the group consisting of:
   A10C, B1C, desB30 human insulin,
   A10C, B2C, desB30 human insulin,
   A10C, B3C, desB30 human insulin,
   A10C, B4C, desB30 human insulin,
   A10C, B1C human insulin,
   A10C, B2C human insulin,
   A10C, B3C human insulin, and
   A10C, B4C human insulin.

4. A method for stabilizing human insulin comprising substituting two or more amino acids of human insulin or desB30 human insulin with cysteine residues, wherein
   a. the three disulfide bonds of human insulin are retained and
   b. the sites of cysteine substitutions are chosen in such a way that the introduced cysteine residues are placed in the three dimensional structure of the folded insulin analogue to allow for the formation of one or more additional disulfide bonds not present in human insulin,
thereby creating a human insulin analogue comprising one or more additional disulfide bonds not present in human insulin.

5. A pharmaceutical composition comprising a biologically active amount of the human insulin analogue according to claim 1 and a pharmaceutically acceptable carrier.

6. A method for the treatment of diabetes mellitus in a subject in need of such treatment, said method comprising administering to the subject a human insulin analogue according to claim 1.

7. An analogue of human insulin according to claim 1, which is selected from the group consisting of:
   A21C, B25C, desB30 human insulin,
   A21C, B26C, desB30 human insulin,
   A21C, B25C human insulin, and
   A21C, B26C human insulin.

8. An analogue of human insulin where the analogue contains one additional disulfide bond not present in human insulin and wherein
   i) the three disulfide bonds of human insulin are retained,
   ii) the amino acid at position A21 of the A chain of human insulin is substituted with a cysteine,
   iii) one amino acid selected from the group consisting of positions B25 and B26 of the B chain of human insulin is substituted with a cysteine, and
   iv) optionally the amino acid at position B30 of human insulin is deleted.

9. An analogue of human insulin according to claim 8, wherein the amino acid at position B25 of the B chain of human insulin is substituted with a cysteine.

10. An analogue of human insulin according to claim 8, wherein the amino acid at position B26 of the B chain of human insulin is substituted with a cysteine.

11. A pharmaceutical composition comprising a biologically active amount of the human insulin analogue according to claim 8 and a pharmaceutically acceptable carrier.

12. A method for the treatment of diabetes mellitus in a subject in need of such treatment, said method comprising administering to the subject a human insulin analogue according to claim 8.

* * * * *